US012799156B2

(12) United States Patent
Wang et al.

(10) Patent No.: US 12,799,156 B2
(45) Date of Patent: Nov. 17, 2026

(54) METHOD FOR ENHANCING SOLUBILITY OF PLANT PROTEIN

(71) Applicant: Jiangnan University, Wuxi (CN)

(72) Inventors: Ren Wang, Wuxi (CN); Zirui Lu, Wuxi (CN); Xuyuan Li, Wuxi (CN); Pengcheng Xu, Wuxi (CN); Wei Feng, Wuxi (CN); Tao Wang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 802 days.

(21) Appl. No.: 18/075,449

(22) Filed: Dec. 6, 2022

(65) Prior Publication Data

US 2024/0051988 A1 Feb. 15, 2024

(30) Foreign Application Priority Data

Aug. 15, 2022 (CN) ......................... 202210973723.4

(51) Int. Cl.
*C07K 1/34* (2006.01)
*C07K 1/14* (2006.01)

(52) U.S. Cl.
CPC ................ *C07K 1/145* (2013.01); *C07K 1/34* (2013.01)

(58) Field of Classification Search
CPC .... C07K 1/145; C07K 1/34; A23J 1/14; A23J 3/16; A23J 3/14
See application file for complete search history.

(56) References Cited

U.S. PATENT DOCUMENTS

2022/0039428 A1* 2/2022 Wang ..................... C07K 1/145

FOREIGN PATENT DOCUMENTS

| | | | | |
|---|---|---|---|---|
| EP | 1145642 | A1 | * | 10/2001 |
| WO | WO2021168221 | A1 | * | 8/2021 |
| WO | WO-2023284184 | A1 | * | 1/2023 |

OTHER PUBLICATIONS

Machine Translation of WO 2023284184 A1 (Year: 2021).*
Firdaous, L; Concentration and selective separation of bioactive peptides from an alfalfa white protein hydrolysate by electrodialysis with ultrafiltration membrane. Journal of Membrane Science, vol. 329, Issues 1-2, 2009, (Year: 2009).*
Jiang et al. pH Shifting Alters Solubility Characteristics and Thermal Stability of Soy Protein Isolate and Its Globulin Fractions in Different pH, Salt Concentration, and Temperature Conditions. J. Agric. Food Chem. 2010, 58, 13, 8035-804 (Year: 2010).*

* cited by examiner

*Primary Examiner* — Robert B Mondesi
*Assistant Examiner* — Dalton Edward Kiefer
(74) *Attorney, Agent, or Firm* — MATTHIAS SCHOLL P.C.; Matthias Scholl

(57) ABSTRACT

A method for enhancing a solubility of a plant protein includes: mixing a plant protein and water, and adjusting the pH value of a resulting mixture of the plant protein and water to 10-12 for dissolution of the plant protein, thereby obtaining a swollen plant protein; treating the swollen plant protein through ion exchange until the pH value of the mixture is 7-8, and filtering the mixture, to yield a first supernatant; separating the first supernatant to yield a second supernatant; and drying the second supernatant, to yield a modified plant protein whose solubility is higher than that of the raw plant protein.

5 Claims, No Drawings

METHOD FOR ENHANCING SOLUBILITY OF PLANT PROTEIN

CROSS-REFERENCE TO RELATED APPLICATIONS

Pursuant to 35 U.S.C. § 119 and the Paris Convention Treaty, this application claims foreign priority to Chinese Patent Application No. 202210973723.4 filed Aug. 15, 2022, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of deep processing of food protein, and more particularly, to a method for enhancing a solubility of a plant protein.

The limited solubility of some plant proteins has hindered the wide application thereof. Conventionally, chemical, enzymatic and physical methods have been developed to enhance the solubility of plant proteins. Enzymatic methods destroy the primary structure of the proteins and lead to a certain bitter taste, reducing the application value of the products. The chemical methods use acid, base or modified groups to destroy the original chemical bonds of proteins to improve the solubility thereof. The physical methods are relatively mild, but they are often used as an auxiliary means to improve the solubility of plant proteins with a limited effect.

SUMMARY

One objective of the disclosure is to provide a method for enhancing a solubility of a plant protein, which is conducive to preparing uniform protein nanoparticles.

The disclosure provides a method for enhancing a solubility of a plant protein, the method comprising:

1) mixing a plant protein and water, and adjusting a pH value of a resulting mixture of the plant protein and water to 10-12 for dissolution of the plant protein, thereby obtaining a swollen plant protein;
2) treating the swollen plant protein through ion exchange until the pH value of the mixture is 7-8, and filtering the mixture, to yield a first supernatant;
3) separating the first supernatant to yield a second supernatant; and
4) drying the second supernatant, to yield a modified plant protein whose solubility is higher than that of the plant protein in 1).

In a class of this embodiment, in 1), the plant protein is soybean protein, corn protein, rice protein, walnut protein or chickpea protein.

In a class of this embodiment, in 1), a ratio of a mass of the plant protein to a volume of the water is 800-1200 g: 18-22 L.

In a class of this embodiment, in 1), the ratio of the mass of the plant protein to the volume of the water is 1000 g: 20 L.

In a class of this embodiment, in 1), the pH value of the mixture of the plant protein and water is adjusted through an alkali solution; and the alkali solution comprises sodium hydroxide.

In a class of this embodiment, in 1), the mixture of the plant protein and water is stirred at 300-2000 rpm for 30-120 min for dissolution.

In a class of this embodiment, in 1), the mixture of the plant protein and water is stirred at 500 rpm for 30 min for dissolution.

In a class of this embodiment, in 2), the ion exchange is hydrogen ion exchange resin adsorption, ultrafiltration or electrodialysis.

In a class of this embodiment, in 3), the first supernatant is separated through centrifugation under a centrifugal force of 3000-10000 g for 1-20 min.

In a class of this embodiment, the centrifugation is carried out under a centrifugal force of 5000 g for 5 min.

The following advantages are associated with the method for enhancing the solubility of a plant protein of the disclosure.

On the basis of retaining the original structure of the plant proteins, the method of the disclosure improves the solubility and particle homogenization of individual plant protein. Specifically, an alkali solution is used to induce the transformation of the molten state of the protein, so that the protein can be dispersed in water. In the process of ion exchange, the renaturation rule of the original protein is changed, thus reducing the renaturation degree of protein, and improving the neutral solubility of the proteins. The plant protein obtained by the method has the characteristics of high solubility and structural homogenization, and has broad application prospects in medicine, food, cosmetics and health products industries.

DETAILED DESCRIPTION OF THE EMBODIMENTS

To further illustrate, embodiments detailing a method for enhancing a solubility of a plant protein are described below. It should be noted that the following embodiments are intended to describe and not to limit the disclosure.

The disclosure provides a method for enhancing a solubility of a plant protein, the method comprising:

1) mixing a plant protein and water, and adjusting a pH value of a resulting mixture of the plant protein and water to 10-12 for dissolution of the plant protein, thereby obtaining a swollen plant protein;
2) treating the swollen plant protein through ion exchange until the pH value of the mixture is 7-8, and filtering the mixture, to yield a first supernatant;
3) separating the first supernatant to yield a second supernatant; and
4) drying the second supernatant, to yield a modified plant protein whose solubility is higher than that of the plant protein in 1).

The method first mixes the plant protein and water, and then adjusts the pH value of the mixture of the plant protein and water to 10-12 for dissolution of the plant protein, to yield the swollen plant protein. The disclosure has no special restriction on the source of plant proteins, and the conventional commercially available products is applicable. For example, in 1), the plant protein is soybean protein, corn protein, rice protein, walnut protein or chickpea protein. Preferably, in 1), a ratio of a mass of the plant protein to a volume of the water is 800-1200 g: 18-22 L. Particularly, in 1), the ratio of the mass of the plant protein to the volume of the water is 1000 g: 20 L. Preferably, in 1), the pH value of the mixture of the plant protein and water is adjusted through sodium hydroxide solution to be 10-12, particularly, 12. In 1), the mixture of the plant protein and water is stirred at 300-2000 rpm for 30-120 min for dissolution, particularly, at 500 rpm for 30 min for dissolution.

The swollen plant protein is further treated through ion exchange until the pH value of the mixture is 7-8, and filtering the mixture, to yield a first supernatant. In the method, the ion exchange is hydrogen ion exchange resin adsorption, ultrafiltration or electrodialysis.

The first supernatant is separated to yield a second supernatant. The separation method comprises centrifugation under a centrifugal force of 3000-10000 g for 1-20 min, particularly, under a centrifugal force of 5000 g for 5 min.

Finally, the second supernatant is dried to yield a modified plant protein whose solubility is higher than that of the plant protein in 1). The disclosure has no special limitation on the drying method, and the conventional drying method in the art is applicable.

Example 1

1) 1000 g of rice protein was dispersed in 20 L of water, and NaOH was added to adjust the pH of the mixture to 11. The mixture was stirred at 500 rpm for 30 min.
2) The obtained alkali solution was loaded to a hydrogen type weak acid cation resin for static adsorption until the pH of the mixture was 7, and the supernatant was collected.
3) The supernatant was centrifuged under a centrifugal force of 3000 g for 20 min, and the supernatant was dried to yield a modified rice protein whose solubility was higher than that of the rice protein in 1).

Example 2

1) 1000 g of zein was dispersed in 20 L of water, and NaOH was added to adjust the pH of the mixture to 12. The mixture was stirred at 1000 rpm for 60 min.
2) The obtained alkali solution was treated through ultrafiltration until the pH of the mixture was 7, and the supernatant was collected.
3) The supernatant was centrifuged under a centrifugal force of 10000 g for 10 min, and the supernatant was dried to yield a zein product.

Example 3

1) 1000 g of glutenin was dispersed in 20 L of water, and NaOH was added to adjust the pH of the mixture to 11. The mixture was stirred at 2000 rpm for 120 min.
2) The obtained alkali solution was treated through electrodialysis until the pH of the mixture was 8, and the supernatant was collected.
3) The supernatant was centrifuged under a centrifugal force of 10000 g for 5 min, and the supernatant was dried to yield a glutenin product.

Comparison Example 1

Conventional rice protein without any treatment.

Comparison Example 2

1) 1000 g of rice protein was dispersed in 20 L of water, and NaOH was added to adjust the pH of the mixture to 11. The mixture was stirred at 500 rpm for 30 min.
2) The obtained alkali solution was mixed with hydrochloric acid until the pH of the mixture was 7, and the supernatant was collected.
3) The supernatant was centrifuged under a centrifugal force of 3000 g for 20 min, and the supernatant was dried to yield a rice protein product.

Comparison Example 3

1) 1000 g of rice protein was dispersed in 20 L of water, and NaOH was added to adjust the pH of the mixture to 9. The mixture was stirred at 500 rpm for 30 min.
2) The obtained alkali solution was loaded to a hydrogen type weak acid cation resin for static adsorption until the pH of the mixture was 7, and the supernatant was collected.
3) The supernatant was centrifuged under a centrifugal force of 3000 g for 20 min, and the supernatant was dried to yield a modified rice protein whose solubility was higher than that of the rice protein in 1).

Comparison Example 4

Conventional zein without any treatment.

Comparison Example 5

1) 1000 g of zein was dispersed in 20 L of water, and NaOH was added to adjust the pH of the mixture to 12. The mixture was stirred at 1000 rpm for 60 min.
2) The obtained alkali solution was mixed with hydrochloric acid until the pH of the mixture was 7, and the supernatant was collected.
3) The supernatant was centrifuged under a centrifugal force of 10000 g for 10 min, and the supernatant was dried to yield a zein product.

Comparison Example 6

1) 1000 g of zein was dispersed in 20 L of water, and NaOH was added to adjust the pH of the mixture to 9. The mixture was stirred at 1000 rpm for 60 min.
2) The obtained alkali solution was treated through ultrafiltration until the pH of the mixture was 7, and the supernatant was collected.
3) The supernatant was centrifuged under a centrifugal force of 10000 g for 10 min, and the supernatant was dried to yield a zein product.

Comparison Example 7

Conventional glutenin without any treatment.

Comparison Example 8

1) 1000 g of glutenin was dispersed in 20 L of water, and NaOH was added to adjust the pH of the mixture to 11. The mixture was stirred at 2000 rpm for 120 min.

2) The obtained alkali solution was mixed with hydrochloric acid until the pH of the mixture was 8, and the supernatant was collected.
3) The supernatant was centrifuged under a centrifugal force of 10000 g for 5 min, and the supernatant was dried to yield a glutenin product.

Comparison Example 9

1) 1000 g of glutenin was dispersed in 20 L of water, and NaOH was added to adjust the pH of the mixture to 9. The mixture was stirred at 2000 rpm for 120 min.
2) The obtained alkali solution was treated through electrodialysis until the pH of the mixture was 8, and the supernatant was collected.
3) The supernatant was centrifuged under a centrifugal force of 10000 g for 5 min, and the supernatant was dried to yield a glutenin product.

Detection Method

The mass ($m_0$) of the raw plant protein and the soluble protein (m) of the treated plant protein were determined using Kjeldahl nitrogen.

The solubility of the proteins is expressed as follows:

$$\text{Protein solubility }(\%)=m/m_0\times 100\%;$$

where: m represents the mass of soluble protein (g);

$m_0$ represents the mass of the raw plant protein (g).

The properties of the protein prepared by Examples and Comparison examples are shown in Table 1:

TABLE 1

| solubility property of proteins | | | | | |
|---|---|---|---|---|---|
| Rice protein | | Zein | | Glutenin | |
| | Solubility/% | | Solubility/% | | Solubility/% |
| Example1 | 90.5 | Example2 | 93.2 | Example3 | 93.8 |
| Comparison example1 | 1.7 | Comparison example4 | 5.7 | Comparison example7 | 3.2 |
| Comparison example2 | 9.3 | Comparison example5 | 11.7 | Comparison example8 | 17.2 |
| Comparison example3 | 35.7 | Comparison example6 | 40.9 | Comparison example9 | 37.5 |

From the above data, it can be seen that the solubility of the plant proteins prepared in the above examples 1-3 has been significantly improved, and the solubility is above 90%. The solubility of the proteins without treatment in Comparison examples 1, 4 and 7 was less than 10%, and the solubility of proteins in Comparison examples 2, 5 and 8 with hydrochloric acid to adjust the pH was also less than 20%. For Comparison examples 3, 6, and 9, the pH of the alkali solution was lower than 9, resulting in inadequate swelling of the protein and therefore lower solubility than corresponding examples. Therefore, the method of the disclosure can effectively improve the solubility of plant proteins.

It will be obvious to those skilled in the art that changes and modifications may be made, and therefore, the aim in the appended claims is to cover all such changes and modifications.

What is claimed is:

1. A method for modifying a plant protein, the method comprising:

(a) mixing a plant protein and water, and adjusting the pH value of the resulting mixture of the plant protein and water to 11 or 12 for dissolution of the plant protein, thereby obtaining a swollen plant protein;

(b) treating the swollen plant protein through hydrogen ion exchange resin adsorption or electrodialysis until the pH value of the mixture is 7 or 8, and filtering the mixture, to yield a first supernatant;

(c) separating the first supernatant to yield a second supernatant; and (d) drying the second supernatant, to yield a modified plant protein; wherein in (a), the ratio of the mass of the plant protein to the volume of the water is 1000 g: 20 L; and the plant protein is a corn protein, a rice protein, a walnut protein, or a chickpea protein.

2. The method of claim 1, wherein in (a), the pH value of the mixture of the plant protein and water is adjusted through an alkali solution; and wherein the alkali solution comprises sodium hydroxide.

3. The method of claim 1, wherein in (a), the mixture of the plant protein and water is stirred at 500 rpm for 30 min, 1000 rpm for 60 min, or 2000 rpm for 120 min for dissolution.

4. The method of claim 1, wherein in (c), the first supernatant is separated through centrifugation under a centrifugal force of 3000 g for 20 min.

5. The method of claim 4, wherein the centrifugation is carried out under a centrifugal force of 10000 g for 5 min or 10 min.

* * * * *